(12) United States Patent
Raje et al.

(10) Patent No.: US 9,044,589 B2
(45) Date of Patent: Jun. 2, 2015

(54) ELECTRODE CONSTRUCTIONS AND METHODS FOR MAKING THE SAME

(75) Inventors: Milind Raje, Wentworthville (AU); Timothy McInnes, Westleigh (AU)

(73) Assignee: Cochlear Limited, Macquarie University, NSW (AU)

( * ) Notice: Subject to any disclaimer, the term of this patent is extended or adjusted under 35 U.S.C. 154(b) by 256 days.

(21) Appl. No.: 13/609,980

(22) Filed: Sep. 11, 2012

(65) Prior Publication Data

US 2014/0074214 A1    Mar. 13, 2014

(51) Int. Cl.
*A61N 1/05*    (2006.01)

(52) U.S. Cl.
CPC ......... *A61N 1/0541* (2013.01); *Y10T 29/49194* (2015.01); *A61N 1/05* (2013.01)

(58) Field of Classification Search
None
See application file for complete search history.

(56) References Cited

U.S. PATENT DOCUMENTS

| | | | |
|---|---|---|---|
| 4,172,451 A * | 10/1979 | Kline | 600/374 |
| 4,484,586 A * | 11/1984 | McMickle et al. | 607/122 |
| 5,016,646 A | 5/1991 | Gotthardt et al. | |
| 5,466,253 A * | 11/1995 | Doan | 607/122 |
| 5,584,873 A * | 12/1996 | Shoberg et al. | 607/122 |
| 5,649,974 A * | 7/1997 | Nelson et al. | 607/122 |
| 5,713,944 A * | 2/1998 | Kroll | 607/122 |
| 7,212,867 B2 * | 5/2007 | Van Venrooij et al. | 607/116 |
| 7,558,632 B1 * | 7/2009 | Salys | 607/125 |
| 7,899,548 B2 | 3/2011 | Barker | |
| 2002/0049485 A1 * | 4/2002 | Smits | 607/122 |
| 2002/0111664 A1 * | 8/2002 | Bartig et al. | 607/122 |
| 2005/0171587 A1 * | 8/2005 | Daglow et al. | 607/116 |
| 2008/0097566 A1 * | 4/2008 | Colliou | 607/122 |
| 2008/0147158 A1 * | 6/2008 | Zweber et al. | 607/122 |
| 2009/0292237 A1 * | 11/2009 | Overstreet et al. | 604/20 |

FOREIGN PATENT DOCUMENTS

WO    8304182 A1    12/1983
WO    2012003297 A1    1/2012

* cited by examiner

*Primary Examiner* — Kennedy Schaetzle
(74) *Attorney, Agent, or Firm* — Lowe Hauptman & Ham, LLP

(57) ABSTRACT

Electrode constructions comprise an inner wall structure with an electrode assembly disposed therein that includes a number of stimulation sites disposed at different locations along its length thereby forming an electrode array. An outer insulating layer is disposed over the electrode assembly and comprises a number of openings disposed therethrough at locations corresponding to the stimulation sites to thereby permit direct contact between the stimulation sites and an adjacent external object.

53 Claims, 10 Drawing Sheets

ELECTRODE CONSTRUCTIONS AND METHODS FOR MAKING THE SAME

FIELD

This disclosure relates to improved electrode constructions and methods for making the same and, more particularly, to an electrode construction comprising an array of electrodes or stimulating sites.

BACKGROUND

Electrode constructions including those used for implanted end-use applications can be used in conjunction for treating certain medical conditions. For example, such electrode constructions are useful for treating certain types of hearing loss, muscular conditions, and neurological conditions. Such electrode constructions typically comprise an array of electrode pads or stimulation sites positioned at certain predetermined locations along the length of the construction. The pads are exposed along the construction and placed into contact adjacent a portion of a recipient's body. For example, for treating hearing loss such stimulation sites are positioned within a recipient's cochlea to replicate sound upon activation of the electrode construction.

Conventionally, such electrode constructions are formed by first positioning each of the electrode pads provided in the form of a piece of metal at the predetermined locations, and then individually connecting each pad to a respective wire by welding process. The bundle of wires attached to the respective pads extends along the length of the electrode construction to a common connection point. Once the pads and wire bundle are formed, completion of the electrode construction involves a number of molding and finishing operations.

A feature of such conventional electrode constructions, inherent in the assembly method of connecting the individual pads to the respective wires by welding process, is the need to remove the insulation on the wire at each electrode pad, and then attach the wire thereto. Additionally, some such conventional electrode constructions require that a strain relief treatment occur at each electrode pad. Such processing steps add complexity and time to the manufacturing process for such conventional electrode constructions.

An additional feature of such conventional electrode constructions is the need to perform a separate helixing step, i.e., spirally running each wire from its pad along the length of the construction to the connection point, for each wire, thereby adding further complexity and time to the manufacturing process. Still further, it is known that the position of the electrode pads can shift and move during the multiple steps, e.g., multiple molding steps and manual assembly steps, used in making such conventional electrode constructions, which shifting and movement is undesired.

SUMMARY

Electrode constructions disclosed herein generally comprise an inner wall structure or sleeve with an electrode assembly disposed thereover. The inner wall structure can have a constant or variable cross-sectional dimension along its length. The electrode assembly comprises a number of stimulation sites disposed at different locations along its length. In an example, each stimulation site comprises a wire-wound construction formed from wire that is wound around the inner wall structure a number of times at a particular inner wall structure location. The stimulation sites form an electrode array extending from a position adjacent a tip of the inner wall structure. The stimulation site can be formed from two or more windings of insulated wire. The inner wall structure or sleeve includes a central cavity that can be filled or unfilled.

The wires used to form the stimulation sites extend from each respective site therefrom along the inner wall structure to a position adjacent a distal end of the inner wall structure. The position can be a common position for all wires extending from respective stimulation sites to facilitate attachment with another device or a connector. The wires can extend from each respective stimulation site along the inner wall structure in a helical fashion or pattern. The pattern and placement of such wire along the length of the inner wall structure can vary to provide flexibility and/or rigidity along the construction. In an example embodiment, the wire used to form a respective stimulation site extends therefrom and past an adjacent stimulation site, wherein the wire may be positioned underneath such adjacent stimulation site.

The electrode construction further includes an outer insulating layer that is disposed over the electrode assembly. The outer insulating layer comprises a number of openings disposed therethrough at locations corresponding to the stimulation sites to thereby permit direct contact between the stimulation sites and an adjacent external object. Electrode constructions as disclosed herein can be provided in the form of an implantable medical device, for example in the form of an implantable component of a hearing prosthesis. In an example, the hearing prosthesis can be a cochlear implant, and in such case the electrode array corresponds to selected placement positions within the human cochlea.

Electrode constructions as disclosed herein avoid the need to provide a separate attachment between wires and contact pads, thereby avoiding the need for any complex strain relief, and are developed in a manner that introduces the ability to provide configuration flexibility in terms of stimulation site placement, number of stimulation sites, stimulation site size and/or surface area, electrode construction stiffness, and electrode construction flexibility.

BRIEF DESCRIPTION OF THE DRAWINGS

These and other features and advantages of electrode constructions and methods for making the same as disclosed herein will be appreciated as the same becomes better understood by reference to the following detailed description when considered in connection with the accompanying drawings.

DETAILED DESCRIPTION

Electrode constructions as disclosed herein are made in a manner that enables the formation of electrode contacts or stimulation sites as an integral part of the respective wires, i.e., from windings of such wires, that are used to transmit stimulation signals from a connection point on the construction to the sites, thereby eliminating the need for individually attaching electrode contacts to wires by welding process and the like as used to make conventional electrode constructions. Additionally, electrode constructions as disclosed herein, comprising one or more stimulation sites, may be formed from a single piece of wire or from a number of different wires, depending on the particular manufacturing approach. Still further, the respective wires used to form the stimulation sites can be helically wound along the length of the electrode construction in a predetermined manner to provide control over an amount of flexibility or stiffness desired at certain locations along the construction.

Figure 1A:
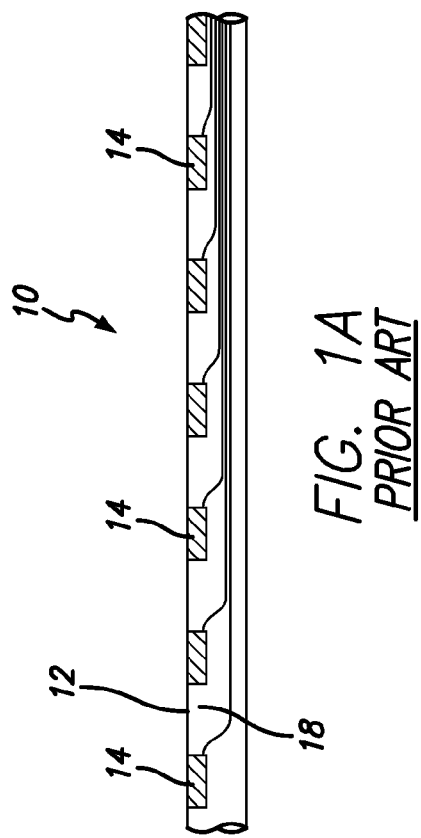
FIGS. 1a and 1b are respective side cross-sectional and side perspective views of a prior art electrode construction.
Figure 1B:
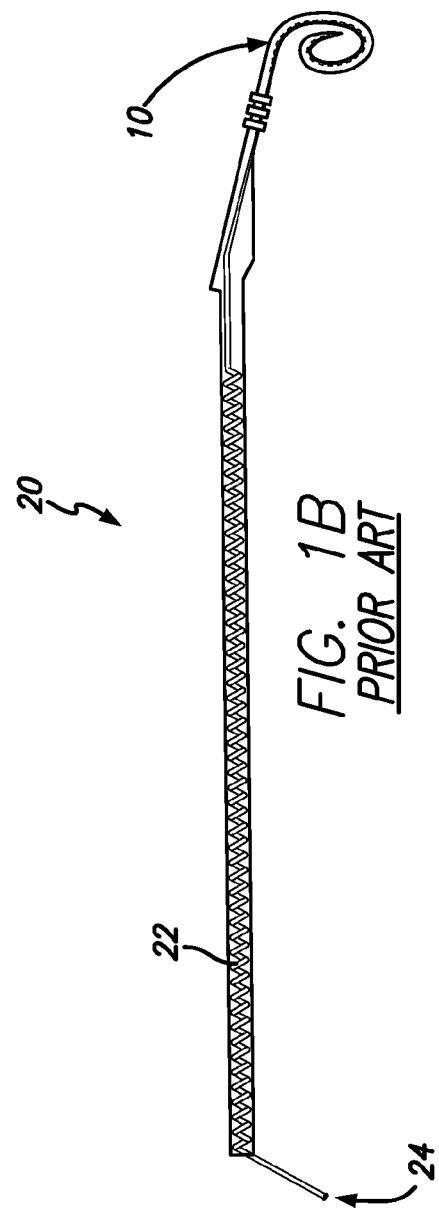

FIGS. 1a and 1b illustrate a conventional electrode construction or an electrode lead. FIG. 1a illustrate a section of the electrode construction 10 adjacent a tip and comprises an outer cover 12 formed from a suitable electrically non-conductive material, and a number of electrode contacts or stimulation sites 14 positioned along the construction extending along a length of the construction from the tip. In such conventional construction, the stimulation sites are formed from preformed metallic pads, e.g., platinum pads, and each of the sites 14 are bonded, by welding, to a respective wire 18 that is used to transfer a stimulation signal from an electrode construction connection point to the site 14. FIG. 1b, illustrates the entire construction 20 including the section 10 illustrated in FIG. 1a. As shown in FIG. 1b, in such conventional construction, the wires 22 connecting each of the sites are bundled together and extend along a length of the electrode construction 20 to a single connection point 24

Figure 2:
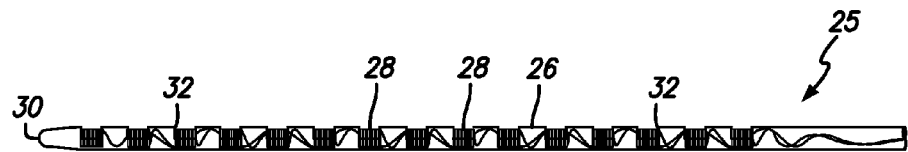
FIG. 2 is a side perspective view of an example electrode construction as disclosed herein.

FIG. 2 illustrates an example electrode construction 25 as disclosed herein comprising an outer cover, carrier or insulating sheath 26 formed from an electrically non-conductive material. In a preferred example, the carrier is formed from a biocompatible material such as silicone or the like. The electrode construction comprises a plurality or an array of electrode contacts or stimulation sites 28 positioned along a length of the construction extending from distal tip 30 therealong. As described in greater detail below, portions of the carrier are removed along the electrode construction to form openings 32 therethrough to permit direct contact between the stimulation sites 28 and an adjacent object when placed thereagainst.

Figure 3:
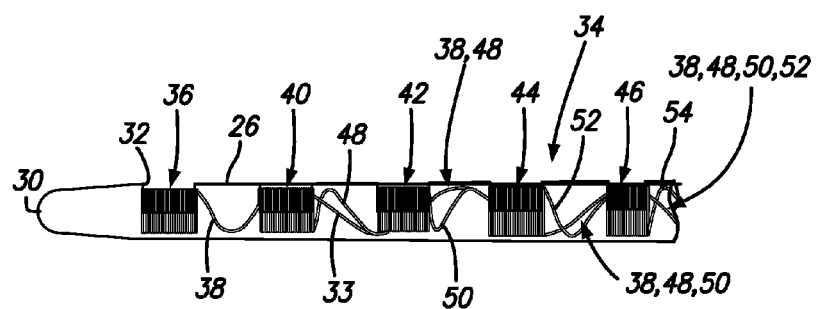
FIG. 3 is a side perspective view of the example electrode construction of FIG. 2 illustrating a stimulation region adjacent a tip portion of the construction.

FIG. 3 illustrates an enlarged view of a stimulating region 34 of the example electrode construction (illustrated in FIG. 2) comprising an array of the stimulation sites extending from the tip 30. The stimulation sites are each formed from a winding of wire, wherein each wire that is wound to form a stimulation site extends therefrom along a length of the electrode construction away from the tip to a connection point. Thus, electrode constructions as disclosed herein comprise a plurality of such stimulation sites that are each formed from a winding of wire, and wherein each wire used to form a respective stimulation site extends therefrom along a length of the electrode construction to a connection point for connection with another device.

Moving from left to right, a first stimulation site 36 is positioned adjacent the tip 30 and is formed from a first winding of wire 38. In an example the wire is formed from an electrically conductive metallic material, and in a preferred example the material is platinum. The wire used to form electrode constructions as disclosed herein can be insulated or non-insulated. In a preferred example, the wire is insulated. However, it is possible to use non-insulated wire in the pre-manufacturing form, in which case alternative insulating means and methods for forming the same are used during the process of making the electrode construction. The wire 38 used to form the first stimulation site 36 extends therefrom within the electrode construction in a spiral fashion past second, third, fourth and fifth stimulation sites, 40, 42, 44, 46, respectively. Each of the second, third, fourth and fifth stimulation sites are formed in a similar manner from a winding of a separate wire, 48, 50, 52 and 54, respectively for each, which wires each extend in a spiral or helically-wound fashion therefrom within the electrode construction.

In an example, the electrode construction can comprise any number of stimulation sites formed in the manner described. The stimulation sites can be positioned and/or sized, e.g., to provide a desired contact surface area, and/or the openings within the carrier can be oriented and sized, as called for by the particular application to perform the desired function of providing a stimulating signal to an adjacent contacting surface. In an example, the wire used to form the electrode construction stimulation sites is insulated, and such insulation is removed in the location of the site during or subsequent to formation of the opening 32 through the carrier 26. Constructed in this fashion, the insulation on the wire operates to prevent any undesired shorts from occurring as the wire used to form the sites passes within the construction along other sites.

In an example, the stimulation sites can be formed from one or more windings of the wire. In a preferred example, it is desired that the stimulation sites be formed from at least two layers of the wire winding. In such example, the insulating material of the second or top most winding of the wire is removed and the insulating material of the first or inner most winding of the wire is preserved, thereby ensuring a desired degree of insulation within the construction. Thus, an advantage of using multiple layers or windings of wires is that when the top layer is ablated away or otherwise removed to expose the stimulation site, the underlying bottom layer provides an insulative barrier that protects the wires running thereunder from electrical short. Also, the use of multiple layers or windings of wire operates to provide mechanical support to the exposed stimulation site should the method used to remove the insulation from the top wire layer also inadvertently remove some of the top layer wire itself.

Another advantage of using multiple layers or windings of the wire for forming the stimulation sites is that it provides additional surface area resulting from small gaps that exist between adjacent wire windings forming a stimulation site. The additional surface area resulting from such gaps between adjacent wires within a winding is additive to the additional surface area that results from forming the stimulation site from wire having a round construction as contrasted with conventional stimulation sites formed from a flat piece of metal. The exposed semicircular shape of each exposed wire, when contrasted to a flat piece of metal, provides such an increased surface area, which can operate to make the stimulation site more effective. In an example, the insulation on the outermost portion of the top layer of wire winding as well as the insulation on a top portion of the underlying layer of wire winding is removed during the process of exposing the stimulation site. The exact number of layers of wire windings used to form the stimulation sites can vary depending such factors as the desired height of the site, e.g., useful to provide a stimulating signal to an adjacent contacting surface, the diameter and size of the wire that is used, and the particular end-use application.

Figure 4:
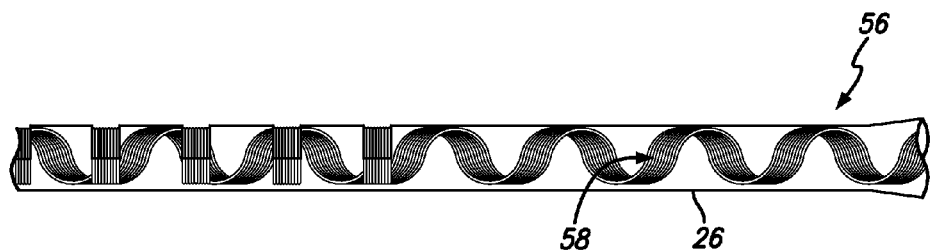
FIG. 4 is a side perspective view of the example electrode construction of FIG. 2 illustrating a covered or shielded region of the construction extending from the stimulator region.

FIG. 4 illustrates an enlarged view of a covered region 56 of the example electrode construction (illustrated in FIG. 2) that does not include stimulation sites, but comprises the carrier 26 as used to cover and insulate the plurality of wires 58 used to form the stimulation sites and that extend in a spiral or helical fashion therein. In an example, the wires extend through the electrode construction and are connected at a single connection point for purpose of providing a mechanical and electrical connection with an external object configured to provide a stimulating signal to the electrode construction.

Figure 5A:
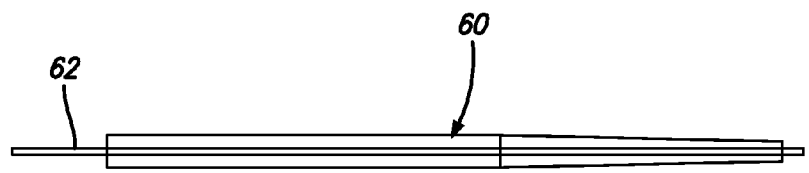
FIGS. 5a to 5k are perspective side views of an example electrode construction at different manufacturing steps.

FIGS. 5a to 5k illustrate electrode constructions as disclosed herein at different stages of being manufactured according to an example method of making. Referring to FIG. 5a, in a first step, a sleeve 60 is disposed onto a cylindrical mandrel 62 and is used to form an inner wall structure for forming the windings of wire thereon. The sleeve can be provided in the form of a preformed, e.g., a preformed, part, or can be formed on the mandrel from dispensing a suitable material thereon that cures or otherwise hardens to form the sleeve. In a preferred, the sleeve is provided in the form of a preformed part and then smoothly the construction can be removed from the mandrel. The preformed part can be configured having a constant or a variable cross-sectional thickness depending on the particular external surface desired for a particular end-use application. The mandrel 62 can be made of metal, plastic or thread. In an example, the mandrel 62 is made from metal and the sleeve 60 is made from a biocompatible polymeric material such as Nusil MED 4860/4213 or the like.

In the illustrated example, the sleeve 60 has a first section defined by a constant cross-sectional thickness, and a second section having a variable cross-sectional thickness that is tapered moving longitudinally therealong. This is but one example sleeve configuration, and it is to be understood that sleeves useful for forming electrode constructions as disclosed here can have a variety of different cross-sectional configurations at different locations depending on the particular end-use application. FIG. 5k illustrates another example electrode construction where the sleeve 60 is configured having a generally tapered cross section moving away from a tip to about half way along the length of the construction, and then having a variable cross section expending within the remaining half of the construction. The different sleeve cross sections can be provided to introduce different levels of flexibly and/or stiffness to the construction to meet needs of the end-use application.

While a sleeve having a circular cross section is illustrated, it is to be understood that sleeves having non-circular cross sections can be used depending on the particular electrode construction end-use application. If desired, the surface of the mandrel can be coated or otherwise treated with a nonstick coating to facilitate removal of the mandrel from the sleeve during a later stage of manufacturing. In an example, the sleeve is sized having a diameter smaller than that of the external diameter of the electrode array.

Figure 5B:
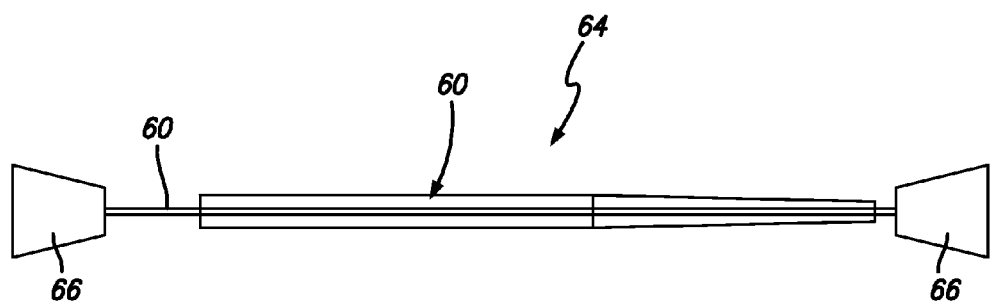
Figure 5C:
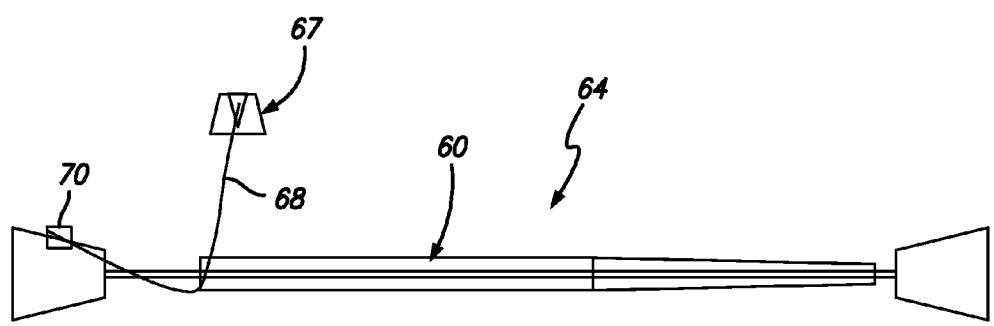

Referring to FIG. 5b, the assembly 64 of the mandrel 62 and the sleeve 60 is tensioned on a winding machine 66. In FIG. 5c, a wire guide 67 is positioned adjacent the assembly 64, wherein the wire guide is configured to dispense wire 68, e.g., disposed on a spool or the like, used to form the stimulation sites onto the sleeve 60. Wire 68 useful for forming electrode constructions as disclosed herein include those formed from conventional metallic materials. In applications where the electrode construction is to be implanted within a recipient, the wire can be coated platinum wire, or wire made from gold or biocompatible metals or metal alloys, such as platinum-iridium or the like. The coating can be formed from polymers such as parylene, sulphone-based polymers, or similar polymers giving desired properties of electrical insulation and physical separation.

The particular diameter size of the wire used can be different and such difference can be used to introduce different features and/or properties to the electrode construction. For example, the diameter of wire selected to make the different stimulation sites can increase moving away from the stimulation sites positioned adjacent the tip, thereby providing both a greater degree of flexibility at and adjacent the tip (e.g., so as to minimize any damage during and after fitment when the end-use application is an implanted medical device), and to provide an increased degree of rigidity away from the tip to provide an improved degree of control during such fitment. Additionally, the use of thicker wire makes for an overall more robust construction. In an example, platinum-iridium wire is used, wherein iridium is used to provide an improved degree of stiffness to the wire.

Figure 5D:
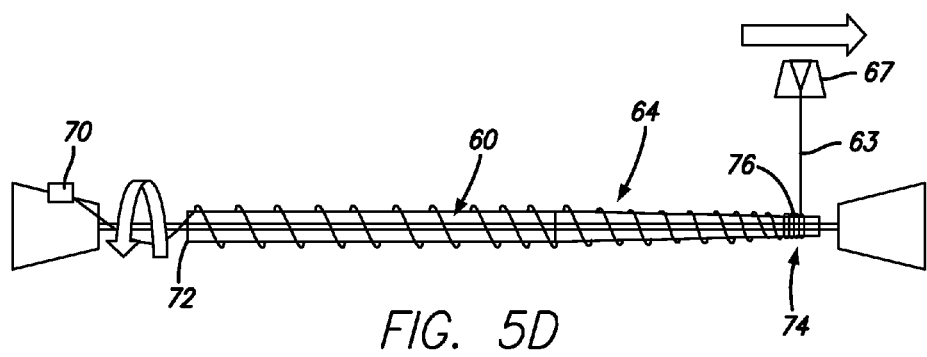

Referring still to FIG. 5c, an end of the wire 68 from the wire guide is 67 is attached to a wire attachment feature or mechanism 70 that rotates with the assembly 64 as the wire guide 67 remains in a non-rotating state, and that is configured to hold the wire in place. The wire guide 67 is configured to move back and forth along the length of the assembly 64. Referring to FIG. 5d, the wire guide 67 moves along the length of the assembly 64 as the assembly is rotated and feeds wire 68 onto the surface of the sleeve 60 so that the wire is disposed thereon in a spiral or helical fashion. If desired, the wire dispensed onto the sleeve can be fed onto through a silicone applicator or the like for the purpose of applying a very thin coating of glue to hold the wires in place over the sleeve. The glue also acts to provide adhesion between individual strands of wire. An example, silicone that can be used for this purpose is MED 4213 from Nusil. Alternate adhesives may be used. Instead of feeding the wire through a silicone applicator, the adhesive material can be applied by brush/spray directly onto the sleeve to thereby provide a desired wire adhesion. Additionally, if the wire used is insulated, the wire can be fed through a device useful for providing an insulating layer thereon prior to being dispensed onto the sleeve.

As shown in FIG. 5.d, the wire guide 67 is moved along length of the sleeve as the sleeve is being rotated to a position on the sleeve. The wire 68 is wound in helical fashion onto the sleeve lengthwise from end 72 adjacent the wire attachment feature 70 to a location on the sleeve adjacent an opposite end that corresponds to the electrode construction first stimulation site. In an example, the sleeve is rotated relative to the wire guide 67 using a lathe-type set up, and the wire 68 is disposed onto the sleeve by the lateral movement of wire guide 67.

Referring still to FIG. 5d, when the first stimulation site location 74 is reached, a desired number of wire windings are wound in serial fashion adjacent one another to provide a desired stimulation site or pad width. The stimulation site width and height or thickness can vary depending on the particular end-use application, thus the following example is provided for reference as it relates to one end-use example where a stimulation site width of approximately 300 microns is desired. In an example, a desired wire 68 useful for making electrode constructions has a thickness of approximately 25 microns, and the desired stimulation site width is achieved by providing a first layer of windings 76 comprising approximately 12 turns of wire wound side-by-side.

Figure 5E:
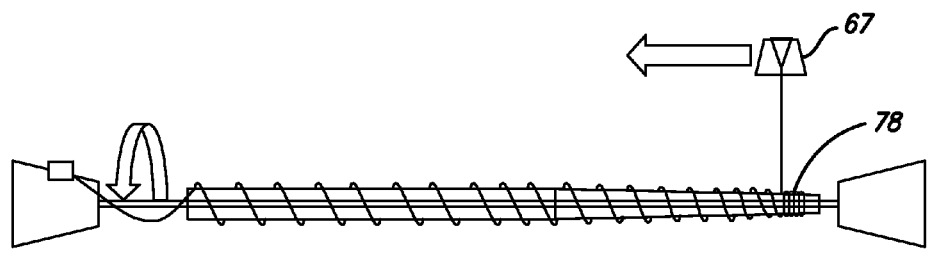

Referring to FIG. 5e, in an example, a desired stimulation site height is approximately 50 microns, and the mandrel and wire guide 67 is operated to provide a second layer of windings 78 comprising another 12 turns of wire so that it overlaps the first set of wire windings to thereby provide the desired first stimulation site height. In a preferred example, once the first stimulation site is formed, the wire used to form the same is then secured into place and is cut before the wire guide 67 is returned to its initial or starting position for forming a subsequent stimulation site.

Figure 5F:
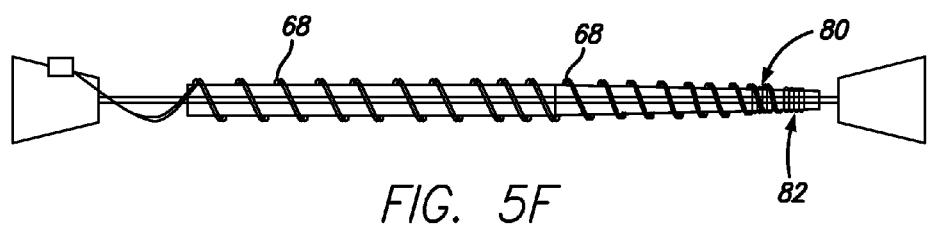

FIG. 5f illustrates the electrode construction after a second stimulation site 80 has been formed in the same manner as the first stimulation site 82. The second stimulation site 80 is formed at a location adjacent the first stimulation site 82. The sequence of forming stimulation sites according the method described above can be repeated as needed for as many stimulation sites called for by the particular end-use application, wherein the wire 68 used to form each stimulation site extends helically from the wire attachment mechanism to its respective stimulation site.

While an example method of making the stimulation sites has been disclosed and illustrated, it is to be understood that other methods of forming the wire-wound stimulation sites are within the scope of the electrode construction as disclosed herein. For example, instead of forming each stimulation site by running wire from an opposite end of the sleeve, the stimulation sites can be formed by starting at the stimulation site location and afterwards running the wire used to form the same helically to the opposite end of the sleeve. Additionally, it is to be understood that the simulation sites as formed herein can be positioned having a uniformly-spaced or non-uniformly spaced arrangement depending on the particular end use application. In a particular example, where the electrode construction is used in conjunction with a cochlear hearing implant system, such construction comprises approximately 22 stimulation sites that are located to make contact against the human cochlea.

Figure 5G:
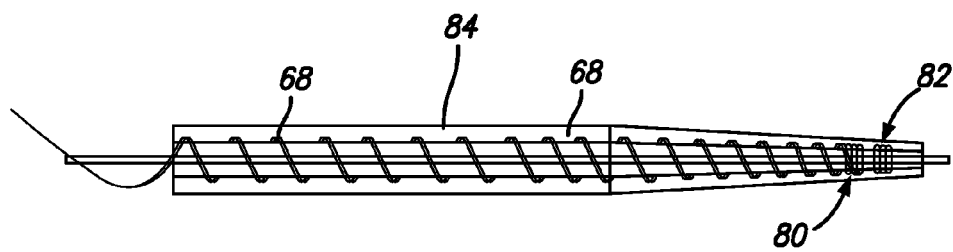

Referring to FIG. 5g, a thin silicone layer 84 is disposed by various means, e.g., by molding, dispensing, dipping, spraying, or the like, over the wires 68 to provide protection and mechanical strength. In an example, the silicone layer is additionally disposed over the stimulation sites 80 and 82. It is also desired that the ends of the wires extending from the sleeve remain exposed to facilitate providing a connection point to further device, e.g., an implant component or the like. Molding or jetting may be used as a method for applying this layer of silicone. The thin silicone structure applied during this step forms the electrode construction external carrier or sheath.

Figure 5H:
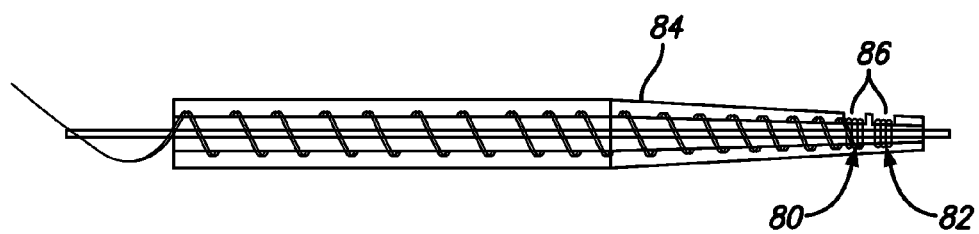

Referring to FIG. 5h, portions of the outer silicone layer 84 are ablated or otherwise removed to provide openings 86 therethrough at positions above each of the stimulation sites 80 and 82 to thereby expose a desired portion of the underlying stimulation sites. During such step, the insulation on the top layer of the wire winding forming each stimulation site is also removed so that the stimulation sites exposed through the openings 84 comprise bare metal wire. The step of ablating can be done by UV or laser treatment, or by mechanical and/or chemical means. The accurate location of the stimulation sites will allow the ablation step to be conducted without use of vision-based machine guiding devices. This is in contrast to conventional stimulation sites made from metal pads that move during the manufacturing process and, thus need a feedback mechanism to determine an exact location to ablate.

Figure 5I:
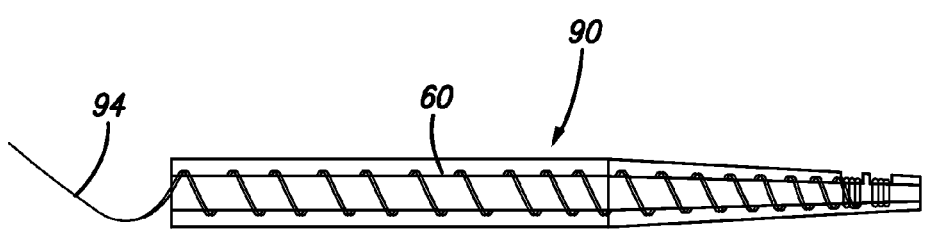

Referring to FIG. 5i, the so-formed electrode construction 90 is removed/slide off of the mandrel, and the loose wire ends 94 extending from the end of the construction are configured to provide the desired mechanical and electrical connection with another device. At the point of its removal from the mandrel, the electrode construction 90 comprises a hollow center cavity as defined by a wall structure of the sleeve 60. The hollow cavity can be filled with a material or left hollow depending on the particular end-use application. For example, the hollow cavity can be filled with a suitable material such as silicone (MED 4880 or similar) to create a straight electrode array. Alternatively the center cavity could be filled with a preformed stiffener, which can be made of metal or a polymer. This may also be formed with a nitinol or similar shape memory alloy on its own or as a combination with silicone. The function of the stiffener is to provide desired rigidity to the electrode construction, and to create a desired final shape. The stiffener may have varying cross section along the length to provide precise control of the above outcomes.

Figure 5J:
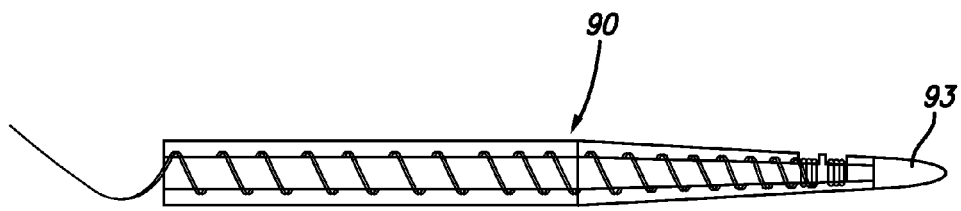
Figure 5K:
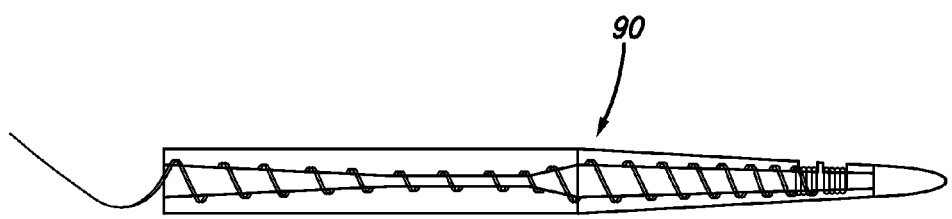

Referring to FIG. 5j, the electrode construction 90 is shown with a tip member 93 attached thereto. The tip member can be formed from a soft material, and can be attached to the electrode construction while it is still attached with the mandrel or after it has been removed therefrom.

If desired, the electrode construction as formed according to the above disclosed method can be molded into a particular shape for its determined end-use application. In an example where the electrode construction is to be used as a cochlear implant, the electrode construction is removed from the mandrel and is placed into a die, e.g., a curved die, replicating the shape of a human cochlea.

While an example method of making electrode constructions has been described above with reference to particular figures and method steps, it is to be understood that electrode constructions as disclosed herein can be made by alternative methods wherein one or more of the above-described steps are combined, or one or more of the above-disclosed steps are broken up or separated into two or more steps, and such alternative methods are intended to be within the scope of this disclosure.

Figure 6A:
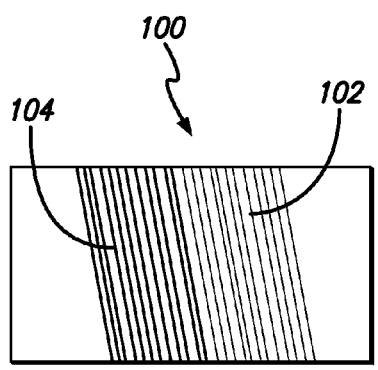
FIGS. 6a and 6B are side perspective views of example electrode construction stimulation sites as disclosed herein.
Figure 6B:
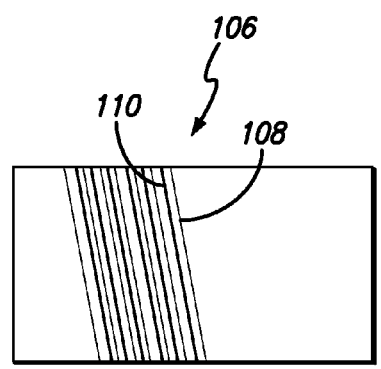

Referring to FIGS. 6a and 6b, electrode constructions as disclosed herein can be configured having stimulation sites comprising two or more different channels, formed by using two or more different wires to form the stimulation site. FIG. 6a illustrates an example two-channel stimulation site example 100 wherein a first channel wire 102 is used to form ½ of the bottom and top windings, and a second channel wire 104 is used to form the other ½ of the top and bottom windings, wherein the two-wire channels are positioned side-by-side of one another. FIG. 6b illustrates another example two-channel example 106 wherein the first and second channel wires 108 and 110 are wound in alternating fashion side-by-side of one another to form both the bottom and top windings, such that the first and second windings comprises a repeated arrangement of the first and second wires. IN such multi-channel examples, the ablation step is carried out in a manner that maintains insulation between the wire windings forming the different channels to ensure that the signals being sent to the different channels do not interfere with one another. These are but a few examples of multi-channel stimulation site examples and others are understood to be within the scope of electrode construction as disclosed herein.

During the step of winding the wire used to form the stimulation site along the length of the mandrel, the pitch of the helical winding can be controlled to provide a desired degree of stiffness or flexibility to the electrode construction. For example, for an application calling for a relatively high degree of flexibility, the pitch of the helical wire winding can be large, for example having a pitch of about 2 mm. In an application calling for a relatively high degree of stiffness, the pitch of the helical wire winding can be small, for example having a pitch of about 0.1 mm as measured relative to the longitudinal axis of the mandrel. Also, the feature of stiffness or flexibility can be engineered to increase in a gradient or step-wise manner within the electrode construction by controlling the pitch of the helical wire winding as needed to achieve the desired result.

Pitch variation by changing the tension and/or spacing during winding can be used to provide the ability to curl the construction in a desired direction and/or orientation during and/or after insertion, e.g., when the construction end-use application is an implanted medical device. This feature can produce an inherent bias internally within the construction that can operate to provide a self-aligning/self-orienting feature to the electrode construction that can be very useful during insertion and/or surgery for proper insertion and fitment orientation, e.g., to help ensure positioning and alignment of the stimulation sites with the desired surface of the cochlea when used as a cochlear implant. Wire tension, wire spacing, wire diameter all contribute to providing such a desired internal bias.

Figure 7A:
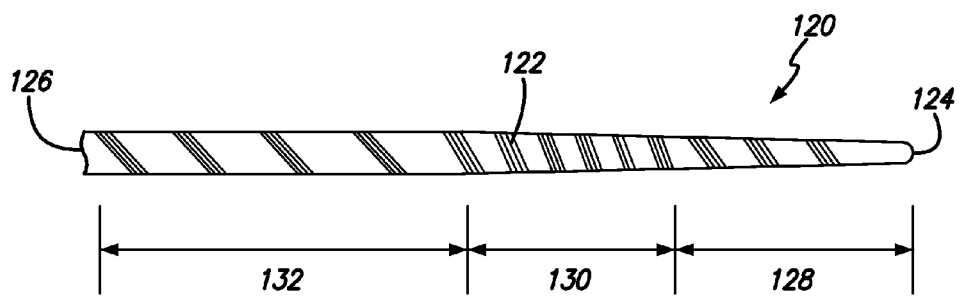
FIGS. 7a to 7c are side perspective views of example electrode construction conducting wire configurations as disclosed herein.
Figure 7B:
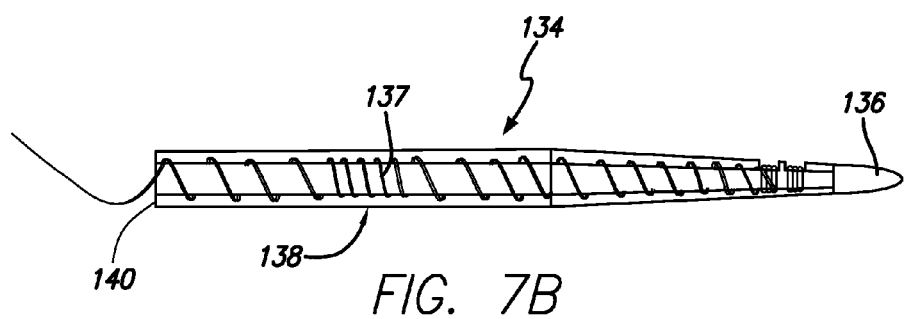
Figure 7C:
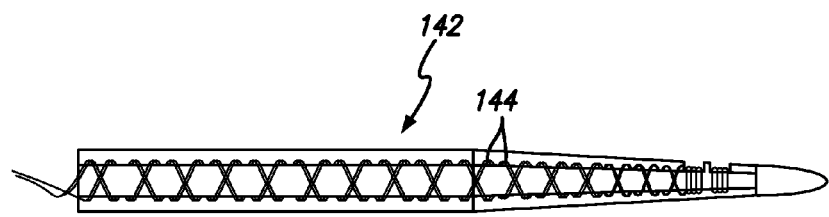

FIGS. 7a to 7c illustrate example electrode constructions with the wire wound with a different pitch to provide different properties of flexibility and stiffness. FIG. 7a illustrates a side view of an example electrode construction 120 showing conduction wires 122 extending therein from a tip 124 to an opposite end 126. The figure helps illustrate how the pitch of the helical conduction wire winding can be controlled to produce an electrode construction having combined features of flexibility in one region and stiffness in another region, e.g., by winding the wire in an large helical pitch in the area where flexibility is desired, and winding the wire in a smaller helical pitch in the area where stiffness is desired. As illustrated, in a first region 128 (extending a distance from the tip 124) the pitch of the helically wound conduction wires is relatively large to provide flexibility. In a second region 130 (extending a distance from the first region 128) the pitch of the helically wound conduction wires is relatively small to provide in increased degree of stiffness. While in a third region 132 (extending from the second region 130 to the end 126) the pitch of the helically wound conduction wires is again relatively large to provide flexibility.

FIG. 7b illustrates another example electrode construction 134 comprising wires wound having a relatively large pitch extending a length from the tip 136 to provide flexibility thereto, and comprising wires 137 wound having a relatively smaller pitch within portion 138 of the construction distant from the tip and adjacent an opposite end 140. FIG. 7c illustrates a still other example electrode construction 142 comprising wires 144 wound in opposite directions to increase the stiffness of the construction. In this particular example, the wire used one stimulation site is wound along the length of the construction in a helical fashion in a direction opposite to a next stimulation site. In addition to the cross winding or braiding of the wires, the pitch of the wires in each winding can also be change to provide further changes in flexibility and/or stiffness as desired for a particular end use application. These are but a few examples of how the pitch and/or orientation of the helically wound wires extending from the stimulation sites can be controlled to provide desired properties of stiffness or flexibility at different locations within the electrode construction, and it is understood that many variations exist and all such variations are within the scope of electrode constructions as disclosed herein.

Figure 8:
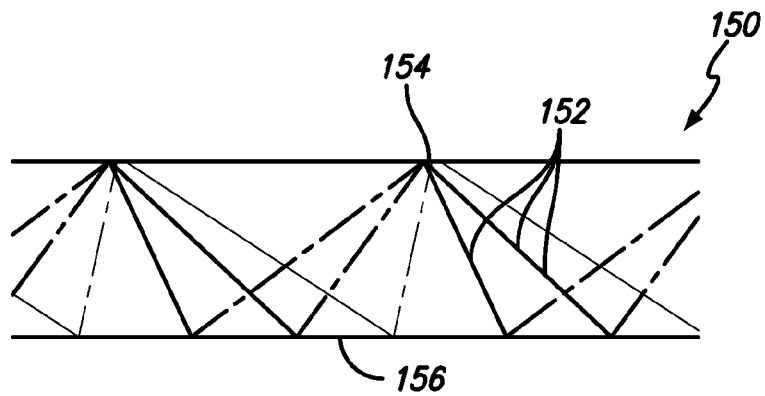
FIG. 8 is a schematic cross-sectional side view of an example electrode construction as disclosed herein.

Additionally, electrode constructions as disclosed herein can be constructed to provide combined properties of stiffness and flexibility at different sections of the same region. FIG. 8 illustrates a schematic side view of an electrode construction 150 wherein the conduction wires 152 used to form the stimulation sites have been bundled at a top section 154 of the construction and distributed along an opposed bottom section 156, thereby providing combined properties of lower stiffness along the top section 154 and higher stiffness along the bottom section 156. This is just one example of how bundling and distribution of the helically wound conduction wires can be used to provide different stiffness properties at different sections of the same region.

Figure 9A:
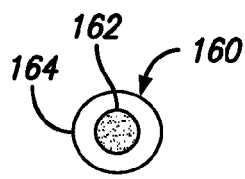
FIGS. 9a to 9e are cross-sectional views of different example electrode constructions as disclosed herein.
Figure 9B:
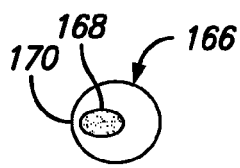
Figure 9C:
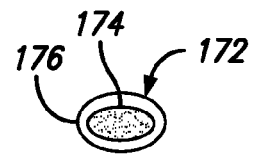
Figure 9D:
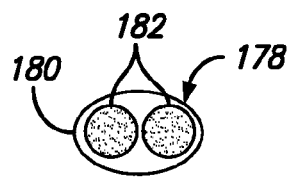
Figure 9E:
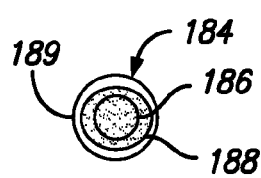

While electrode constructions have been disclosed herein as comprising a particular internal configuration, it is to be understood that electrode constructions comprising wire wound stimulation sites can be embodied having different internal configurations. FIGS. 9a to 9e, illustrate cross sections of example electrode constructions having different internal configurations. FIG. 9a illustrates an electrode construction 160 comprising a generally circular sleeve 162 and a generally circular outer layer 164 disposed over the various wire-wound stimulation sites (not shown) and respective conduction wires (not shown). FIG. 9b illustrates an electrode construction 166 comprising an oval sleeve 168 positioned non-concentrically within a generally circular outer layer 170 disposed over the various wire-wound stimulation sites (not shown) and respective conduction wires (not shown). FIG. 9c illustrates an electrode construction 172 comprising an oval sleeve 174 positioned concentrically within an oval outer layer 176 disposed over the various wire-wound stimulation sites (not shown) and respective conduction wires (not shown). FIG. 9d illustrates an electrode construction 178 comprising a pair of sleeves 180 positioned within a generally oval outer layer 182, wherein each sleeve is constructed having one or more wire-wound stimulation sites (not shown) formed thereon. FIG. 9e illustrates an electrode construction 184 comprising two concentrically arranged sleeves 186 and 188, wherein each sleeve includes one or more wire-wound stimulation site formed thereon, and an outer layer 189 disposed thereover. These are but a few variations on the internal configuration of electrode constructions as disclosed here, and it is understood that other variations exist and are within the scope of the electrode construction as disclosed herein.

Features of stimulation sites formed from wire windings as contrasted with conventional stimulation sites formed from a piece of metal include an improved degree of mechanical flexibility, increased surface area by virtue of the surface area and texture of each of the wires used to form the site, and an integral connection to the conductor, i.e., the wire used to form and extending to and from the stimulation site, without any secondary joining processes, e.g., without welding attachment or the like.

A feature of using more than one layer of wire windings to form the stimulation sites is that the first or underlying layer acts as a protective barrier to the laser light or other means used to ablate both the electrode construction outer sheath and the wire coating from the second layer of wire winding used to form the stimulation site. This operates to protect the internal conductors, or the wires running underneath of the stimulation sites used to form other downstream stimulation sites, from undesired shorts. Additionally, the multilayer arrangement also operates to provide strength and durability against any material loss that may occur during use of the electrode construction and stimulation.

A further feature of forming the stimulation sites from the wire windings as disclosed herein, as contrasted with conventional electrodes having plate stimulation sites attached with a conduction wire, is that the stimulation site does not move during manufacturing. Once the stimulation site is formed, it remains fixed relative to the mandrel and does not move during subsequent manufacturing steps. This feature is desired as it facilitates accurate ablation and removal of the overmolded cover to form a cover to expose the stimulation site, which does not need visual confirmation. Thus, the step of ablating and forming the openings to expose the stimulation site is one that can be performed automatically to increase manufacturing efficiency.

Figure 10:
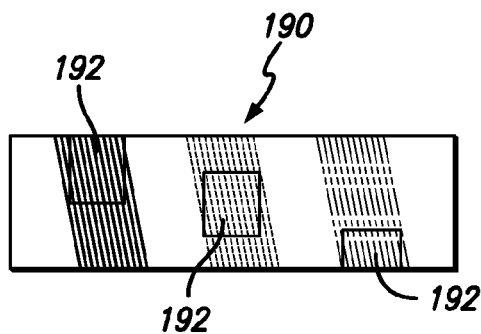
FIG. 10 is a illustrates a side sectional view of an example electrode construction as disclosed herein.

During the step of ablating the outer carrier or sheath to form the openings to expose the stimulation sites the openings that are formed can be controlled so as to expose a desired surface area of the stimulation sites. For example, when the electrode construction is provided in a cylindrical shape, the openings can be formed to expose a desired arc segment (width and length) of the stimulation site, e.g., about 10 to 100 percent, 20 to 80 percent, and 30 to 60 percent of the construction diameter. In an example, where the electrode construction is used in conjunction with a cochlear implant system, it is desired that the opening that exposes the stimulation site comprise about ½ of the construction diameter. It is to be understood that the openings can be positioned anywhere along the stimulation site to provide the desired stimulation site access, e.g., at any cylindrical location, and are not necessarily limited to being positioned at the cylindrical same location and of the same size for a particular electrode construction. FIG. 10 illustrates a section of an example electrode construction 190 demonstrating a few different locations where the stimulation sites 192 and their respective openings can be positioned.

Figure 11:
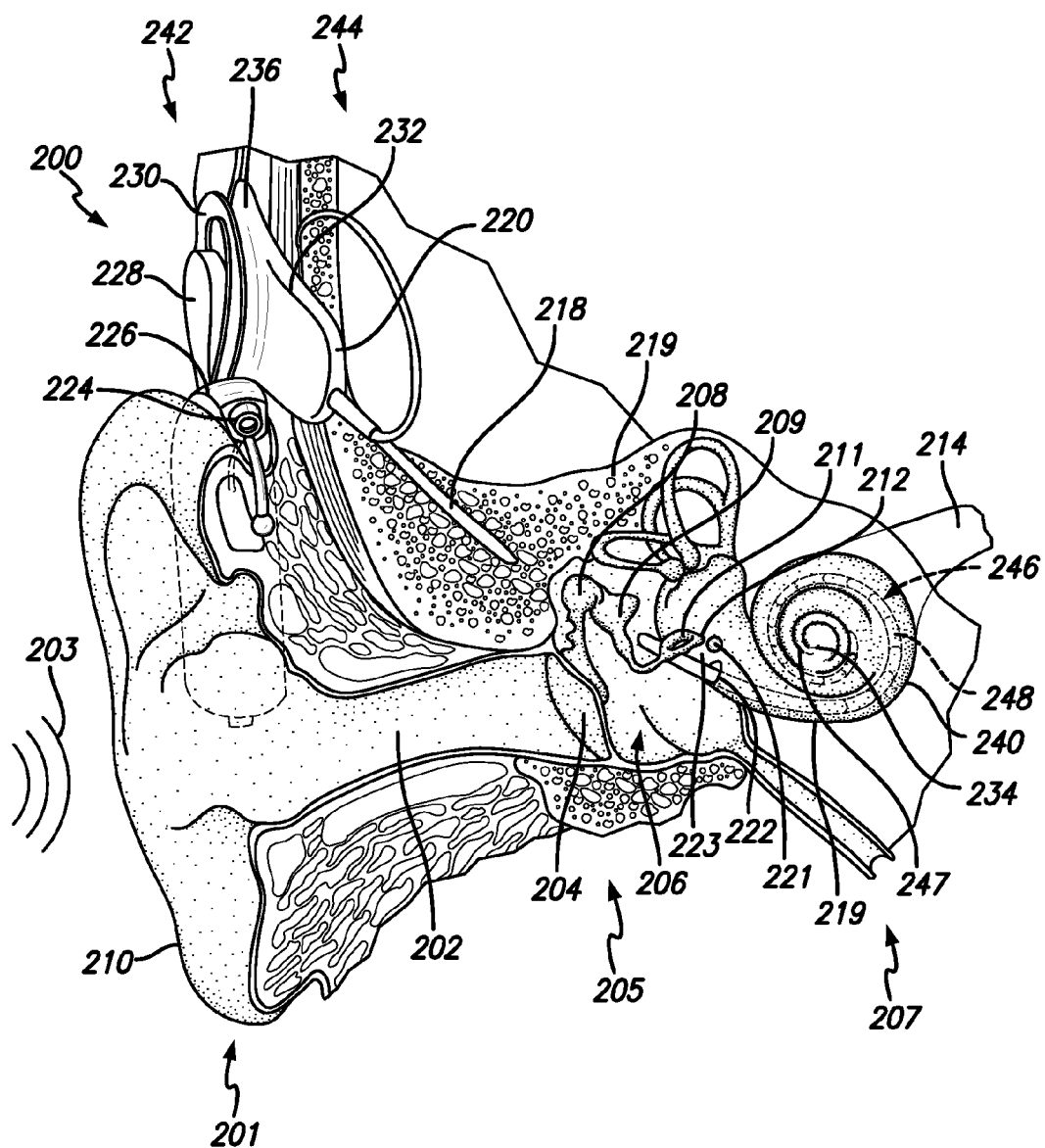
FIG. 11 is a perspective view of a cochlear implant system.

FIG. 11 illustrates a cochlear implant system 200 includes an internal component 244 typically having an internal receiver/transceiver unit 232, a stimulator unit 220, and an elongate stimulating assembly 218 comprising the electrode construction as disclosed herein. The internal receiver/transceiver unit 232 permits the cochlear implant system 200 to receive and/or transmit signals to an external device 226 and includes an internal coil 236, and preferably, a magnet (not shown) fixed relative to the internal coil 236. Internal receiver unit 232 and stimulator unit 220 are hermetically sealed within a biocompatible housing, sometimes collectively referred to as a stimulator/receiver unit. The magnets facilitate the operational alignment of the external and internal coils, enabling internal coil 236 to receive power and stimulation data from external coil 230.

Elongate stimulating assembly 218 has a proximal end connected to stimulator unit 220, and a distal end implanted in cochlea 240. Stimulating assembly 218 extends from stimulator unit 220 to cochlea 240 through mastoid bone 219. In certain examples, external coil 230 transmits electrical signals (e.g., power and stimulation data) to internal coil 236 via a radio frequency (RF) link, as noted above. Internal coil 236 is typically a wire antenna coil comprised of multiple turns of electrically insulated single-strand or multi-strand platinum or gold wire. The electrical insulation of internal coil 236 is provided by a flexible silicone molding (not shown). In use, implantable receiver unit 232 may be positioned in a recess of the temporal bone adjacent auricle 210 of the recipient. Various types of energy transfer, such as infrared (IR), electromagnetic, capacitive and inductive transfer, may be used to transfer the power and/or data from external device to cochlear implant.

Figure 12:
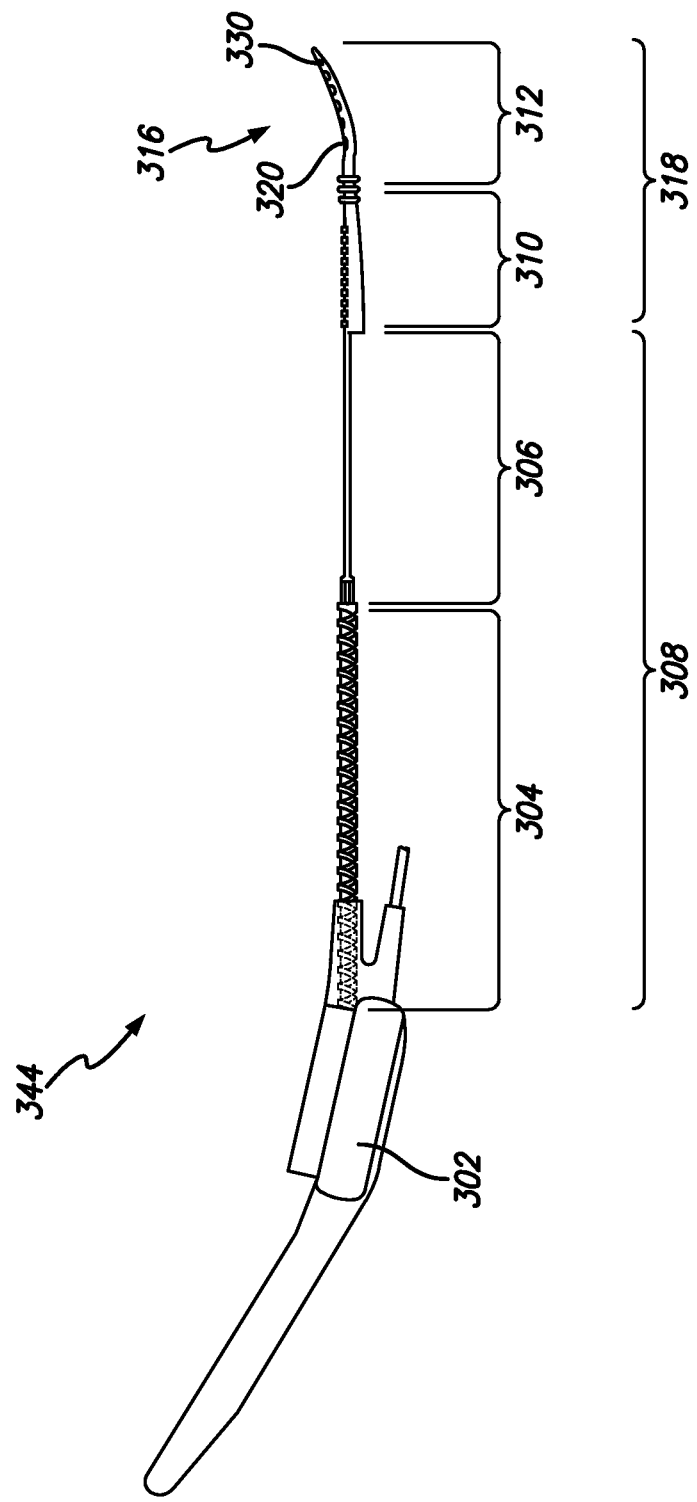
FIG. 12 is a perspective side view of an electrode construction used with the cochlear implant system of FIG. 11.

FIG. 12 is a simplified side view of an internal component 344 having a stimulator/receiver unit 302 which receives encoded signals from an external component of the cochlear implant system. Internal component 344 terminates in a stimulating assembly 318 comprising the electrode construction as disclosed herein. The stimulating assembly comprises an extra-cochlear region 310 and an intracochlear region 312. Intra-cochlear region 312 is configured to be implanted in the recipient's cochlea and has disposed thereon an electrode contact array 316 formed from the stimulation sites as disclosed above. In the present example, contact array 316 comprises both optical contacts 320 and electrical contacts 330. Present commercial devices offered by the industry use electrical contacts, but Cochlear and others are engaged in research on the potential uses of optical stimulation alone of in conjunction with electrical or other stimulation mechanisms.

There are a variety of types of intra-cochlear stimulating assemblies including short, straight and perimodiolar. Perimodiolar stimulating assembly 318 is configured to adopt a curved configuration during and or after implantation into the recipient's cochlea. To achieve this, in certain arrangements, stimulating assembly 318 is pre-curved to the same general curvature of a cochlea. Such examples of stimulating assembly 318, are typically held straight by, for example, a stiffening stylet (not shown) or sheath which is removed during implantation, or alternatively varying material combinations or the use of shape memory materials, so that the stimulating assembly may adopt its curved configuration when in the cochlea. Other methods of implantation, as well as other stimulating assemblies which adopt a curved configuration, may be used. Stimulating assembly 318 can also be a non-perimodiolar stimulating assembly. For example, stimulating assembly 318 may comprise a straight stimulating assembly or a mid-scala assembly which assumes a midscale position during or following implantation. Alternatively, stimulating the stimulated assembly may be a short electrode implanted into at least in basal region. The stimulating assembly may extend towards apical end of cochlea, referred to as cochlea apex. In certain circumstances, the stimulating assembly may be inserted into cochlea via a cochleostomy. In other circumstances, a cochleostomy may be formed through round window, oval window, the promontory or through an apical turn of cochlea.

Internal component 344 further comprises a lead region 308 coupling stimulator/receiver unit 302 to stimulating assembly 318. Lead region 308 comprises a region 304 which is commonly referred to as a helix region, however, the required property is that the lead accommodate movement and is flexible, it does not need to be formed from wire wound helically. Lead region also comprises a transition region 306 which connects helix region 304 to stimulating assembly 318. As described below, optical and/or electrical stimulation signals generated by stimulator/receiver unit 302 are delivered to contact array 316 via lead region 308. Helix region 304 prevents lead region 308 and its connection to stimulator/receiver 302 and stimulating assembly 318 from being damaged due to movement of internal component 144 (or part of 144) which may occur, for example, during mastication.

Certain examples of electrode constructions and methods for making the same have been disclosed. While each such electrode constructions and methods been described with respect to a limited number of examples, the specific features of one example electrode construction should not be attributed to other examples of the electrode construction. No single example is representative of all aspects of electrode constructions and methods of making the same as disclosed herein. In some examples, the electrode construction or method for making the same may comprise features or steps not mentioned herein. Variations and modifications from the described examples exist. The methods of making electrode constructions are described herein as comprising a number of acts or steps. These steps or acts may be practiced in any sequence or order unless otherwise indicated. Finally, any number disclosed herein should be construed to mean approximate, regardless of whether the word "about" or "approximately" is used in describing the number. The appended claims intend to cover all those modifications and variations as falling within the scope of the electrode constructions and methods for making the same as disclosed herein.

What is claimed is:

1. A cochlear implant system comprising:
an external device; and
an implantable internal component comprising an electrode construction, the electrode construction comprising;
a number of stimulation sites positioned at different locations along a length of the construction, wherein each stimulation site is formed from a winding of wire around an inner sleeve, wherein the wire used to form each respective stimulation site extends therefrom to another location of the construction; and
an outer cover formed from an electrically-nonconductive material, the outer cover comprising a number of openings disposed therethrough that are positioned over the stimulation sites to expose a portion of the wire winding used to form the same for making contact with an adjacent surface.

2. The cochlear implant system as recited in claim 1 wherein the wire extending from a respective stimulation site extends in a helical pattern having a pitch that changes along the length of the construction.

3. The cochlear implant system as recited in claim 1 wherein the sleeve has an outer diameter that changes along the length of the construction.

4. The cochlear implant system as recited in claim 1 wherein at least one of the stimulation sites is formed from windings of two or more different wires.

5. The cochlear implant system as recited in claim 1 wherein at least one of the stimulation sites is formed from two layers of wire windings.

6. The cochlear implant system as recited in claim 1 wherein the stimulation sites are positioned for placement within a human cochlea.

7. An electrode construction comprising:
an inner wall structure;
an electrode assembly comprising a number of stimulation sites disposed at different locations along a length of the inner wall structure, wherein each stimulation site comprises a wire-wound construction formed from wire that is wound around the inner wall structure a number of times at a particular inner wall structure location, wherein the wires used to form the stimulation sites extend therefrom along the inner wall structure to a position adjacent a distal end of the inner wall structure; and
an outer insulating layer disposed over the electrode assembly and comprising openings therethrough at locations corresponding to the stimulation sites to permit direct contact between the stimulation sites and an adjacent external object.

8. The construction as recited in claim 7 wherein the stimulation site comprises two or more layers of wire winding.

9. The construction as recited in claim 7 wherein each stimulation site is formed from a separate wire winding.

10. The construction as recited in claim 7 wherein the wire used to form at least one of the stimulation sites extends along the inner wall structure and past a position of an adjacent stimulation site.

11. The construction as recited in claim 7 wherein the number of stimulation sites forms an electrode array extending from a position adjacent a tip of the inner wall structure opposite the distal end.

12. The construction as recited in claim 11 wherein the electrode construction is part of a cochlear implant and the location of the stimulation sites in the electrode array corresponds to selected placement positions within the human cochlea.

13. The construction as recited in claim 7, wherein the electrode construction is an implantable medical device, and the implantable medical device is part of a hearing prosthesis.

14. The construction as recited in claim 7 wherein the wire used to form a stimulating site downstream from an adjacent stimulating site extends underneath of the wire winding used to form the adjacent stimulating site.

15. The construction as recited in claim 7 wherein the wires extend in a helical pattern from respective stimulation sites, and wherein the pitch of the helical pattern is constant along the length of the construction.

16. The construction as recited in claim 7 wherein the wires extend in a helical pattern from respective stimulation sites, and wherein the pitch of the helical pattern changes along the length of the construction.

17. The construction as recited in claim 7 wherein the inner wall structure has a constant cross-sectional thickness extending along its length.

18. The construction as recited in claim 7 wherein the inner wall structure has a variable cross-section thickness extending along its length.

19. The construction as recited in claim 7 wherein the direct contact between the stimulation sites and the adjacent external object is direct contact between respective wire-wound construction of the respective stimulation sites and the adjacent external object.

20. The construction as recited in claim 7 wherein the number of times per unit length along the inner wall structure that the wire is wound about the inner wall structure at a respective stimulation site is substantially greater than the number of times per unit length along the inner wall structure that the wire is wound about the inner wall structure as the wire extends away from the respective stimulation site.

21. An implantable electrode construction comprising:
an electrode array disposed along an inner sleeve, the electrode array comprising:
a number of stimulation sites positioned at different locations along the length of the sleeve, wherein each stimulation site is formed from a winding of wire around the sleeve, the winding having a desired width and thickness; and
a number of wire leads extending along the sleeve, wherein the wire leads extend from and are integral with respective stimulation sites that are formed therefrom, and wherein the wire leads extend from respective stimulation sites to a position adjacent an end of the electrode construction;

an insulating sheath disposed over the electrode array and forming an outer surface of the construction, wherein the insulating sheath comprises a number of openings disposed therethrough and positioned to expose a desired surface area of the stimulation sites to an adjacent object surface.

22. The construction as recited in claim 21 wherein the electrode array is part of an electrode stimulating assembly and the stimulation sites are configured for use with a hearing prosthesis.

23. The construction as recited in claim 21 wherein the stimulations sites are positioned for use within a human cochlea.

24. The construction as recited in claim 21 wherein the sleeve has a cross-sectional thickness that is different at different locations along the sleeve.

25. The construction as recited in claim 21 wherein the construction has a tapered outer configuration.

26. The construction as recited in claim 21 wherein each stimulation site is formed from a different wire.

27. The construction as recited in claim 21 wherein one or more of the stimulation sites is formed from windings of two or more different wires.

28. The construction as recited in claim 21 wherein the pitch of the helical pattern along the length of the sleeve is constant.

29. The construction as recited in claim 21 wherein the pitch of the helical pattern along the length of the sleeve changes.

30. The construction as recited in claim 21 wherein the desired surface area of the stimulation sites is made up of the respective winding of wires forming the respective stimulation site.

31. The construction as recited in claim 21 wherein a number of times per unit length along the sleeve that the wire is wound about the sleeve at a respective stimulation site is substantially greater than the number of times per unit length along the sleeve that the wire is wound about the sleeve as the wire extends away from the respective stimulation site.

32. A method for making an electrode construction comprising the steps of:
    forming a number of stimulation sites along an inner wall structure by winding wire a number of times around the inner wall structure at different locations along the length of the inner wall structure, each stimulation site having a defined width and thickness;
    running wire leads along the inner wall structure from the stimulation sites to a common position on the electrode construction;
    covering the stimulation sites with an insulating material; and
    exposing a surface area of the stimulation sites by removing a section of the insulating material residing above the stimulation site.

33. The method as recited in claim 32 wherein the step of forming comprises using a different wire to form each stimulation site.

34. The method as recited in claim 32 wherein during the step of running, the wire leads extend in a helical pattern along the inner wall structure.

35. The method as recited in claim 32 wherein during one or both of the steps of forming and running, the stimulation sites and wire leads are configured to produce a degree of rigidity, flexibility, or orientation bias to the construction.

36. The method as recited in claim 35 wherein the construction has an orientation bias.

37. The method as recited in claim 36 wherein the orientation bias provides a self-aligning function when the construction is implanted during a surgical procedure.

38. The method as recited in claim 32 wherein the construction has a generally cylindrical outer configuration, and wherein during the step of providing, the removed section is in the range of from about 20 to 80 percent of the construction diameter.

39. The method as recited in claim 32 wherein during the step of forming, each stimulation site has a thickness of at least two wire layers.

40. The method as recited in claim 32 wherein during the step of exposing, an electrically insulating layer covering the wire used to form the stimulation sites is removed.

41. The method as recited in claim 32 wherein after the step of exposing, molding the construction into a desired shape.

42. The method as recited in claim 32 wherein the step of forming comprises winding a respective wire a substantially greater number of times per unit length along the inner wall structure around the inner wall structure at a respective stimulation site than that which is associated with respective wire leads of the wire leads run along the inner wall structure from the respective stimulation sites to the common position.

43. The method of claim 32 wherein the exposed surface area of the respective stimulation sites is made up of the respective wound wires forming the respective stimulation site.

44. A method for making an electrode construction comprising the steps of:
    forming a number of stimulation sites along an inner sleeve by winding wire a number of times around the sleeve at different locations along the length of the sleeve, each stimulation site having a defined width and thickness, wherein the wire used to form each stimulation site extends therefrom along a length of the construction;
    covering the stimulation sites with an insulating material; and
    forming openings through the insulating material to expose a desired surface area of an underlying stimulation site.

45. The method as recited in claim 44 wherein the step of forming comprises dispensing the wire onto the sleeve and moving one longitudinally relative to the other to extend the wire in a helical fashion along the sleeve to a location corresponding to the stimulation site.

46. The method as recited in claim 44 wherein during the step of forming, changing the pitch of the helically wound wire to provide a desired stiffness, flexibility, shape, or orientation bias.

47. The method as recited in claim 44 wherein one or more stimulation sites comprises two layers of wire windings.

48. The method as recited in claim 44 wherein during the step of forming, the wire used to form a previously formed stimulation site extends therefrom and is disposed beneath the wire windings used to form a subsequently formed stimulation site.

49. The method as recited in claim 44 where during the step of forming openings, an electrically insulating layer on the wire is removed from the exposed stimulation site.

50. The method as recited in claim 44 wherein the step of forming comprises dispensing the wire onto the sleeve and moving one of the wire or the sleeve relative to the other of the wire or the sleeve to extend the wire in a helical fashion along the sleeve to a location corresponding to the stimulation site.

51. The method as recited in claim 44, further comprising:
    after the step of exposing, molding the construction into a desired shape.

52. The method as recited in claim 44, further comprising the step of extending respective wires of respective stimulation sites away from the respective stimulation sites, wherein the step of forming comprises winding a respective wire a substantially greater number of times per unit length along the sleeve around the sleeve at a respective stimulation site than that which is associated with that which is the case as the wire extends away from the respective stimulation site.

53. The method of claim 44 wherein the desired surface area of the stimulation sites is made up of the respective wound wires forming the respective stimulation site.

* * * * *